United States Patent [19]

Drukier

[11] Patent Number: 5,532,122
[45] Date of Patent: Jul. 2, 1996

[54] QUANTITATION OF GAMMA AND X-RAY EMITTING ISOTOPES

[75] Inventor: Andrzey K. Drukier, Greenbelt, Md.

[73] Assignee: BioTraces, Inc., Fairfax, Va.

[21] Appl. No.: 133,919

[22] Filed: Oct. 12, 1993

[51] Int. Cl.⁶ ............ C12Q 1/68; G01N 23/00; G01N 33/534; G01T 1/00
[52] U.S. Cl. ............ 435/5; 250/303; 424/1.11; 435/6; 435/7.1; 435/7.2; 435/7.22; 435/7.23; 435/7.31; 435/7.32; 435/7.36; 436/56; 436/57; 436/504; 436/542; 436/545; 436/804; 436/807
[58] Field of Search ............ 435/5, 6, 7.1, 7.2, 435/7.22, 7.23, 7.31, 7.32, 7.36; 436/57, 504, 545, 804, 542, 807; 250/303; 530/391.3; 536/25.32; 424/1.11, 9, 9.1; 422/56

[56] References Cited

U.S. PATENT DOCUMENTS

| | | | |
|---|---|---|---|
| 3,924,125 | 12/1975 | Murray | 250/303 |
| 3,974,088 | 8/1976 | Cofey | 252/644 |
| 4,005,292 | 1/1977 | Osterlin et al. | 250/364 |
| 4,016,418 | 4/1977 | Horrocks et al. | 250/252 |
| 4,444,744 | 4/1984 | Goldenberg et al. | 424/1.49 |
| 4,563,419 | 1/1986 | Ranki et al. | 435/6 |
| 4,682,604 | 7/1987 | Fymat et al. | 128/659 |
| 4,683,195 | 7/1987 | Mullis et al. | 435/6 |
| 4,983,841 | 1/1991 | Stewart et al. | 250/358.1 |
| 5,083,026 | 1/1992 | Elbaum | 250/369 |
| 5,285,073 | 2/1994 | Schelten et al. | 250/394 |

OTHER PUBLICATIONS

Avignone, et al., "Search for the double–B decay of germanium–76", The American Physical Society, vol. 34, No. 2, Aug. 1986, pp. 666–677.

Brodzinski, et al., "Achieving Ultralow Background in a Germanium Spectrometer", Journal of Radioanalytical and Nuclear Chemistry, Articles, vol. 124, No. 2 (1988), pp. 513–521.

Brodzinski, et al., "The Impact of Natural Radioactivity in Solder on Low Backgroung Experiments", Nuclear Instruments and Methods in Physics Research A254 (1987), pp. 472–473.

Primary Examiner—David Saunders
Attorney, Agent, or Firm—Michael A. Gollin

[57] ABSTRACT

For isotopes decaying by capture of an inner shell electron by the nucleus, coincident emission of X-ray and gamma photons may occur. The X-ray results from the drop of an outer shell electron to fill the S shell. The gamma results from the transition of the excited daughter nucleus to a lower energy state. The invention disclosed is a Coincident Gamma and X-ray Detector (CGXD) which achieves extraordinary background rejection by a synergistic combination of coincident counting and other background suppression measures. Whereas the background registered by single gamma counters is of the order of 20–40 counts per minute, a CGXD optimized for the electron capture radio-isotope $I^{125}$ has a background of about one count per day.

91 Claims, 2 Drawing Sheets

QUANTITATION OF GAMMA AND X-RAY EMITTING ISOTOPES

BACKGROUND OF THE INVENTION

The present invention relates to methods for detecting a coincident gamma and X-ray emitting isotope in a sample. More specifically, the invention relates to detecting coincident gamma and X-ray emissions from electron capture (EC) isotopes, while combining coincident counting and other background rejection measures to achieve extraordinary sensitivity.

SUMMARY OF THE INVENTION

According to the invention, a method for detecting a coincident gamma/X-ray (CGX) emitter in a sample comprises detecting coincident gamma and X-ray radiation from the CGX emitter as output pulses in separate radiation detectors, analyzing the shape and height of the pulses on-line to identify pulses characteristic of single photon emissions, discriminating and rejecting non-coincident gamma and X-ray radiation and spurious pulses, suppressing background radiation by shielding the detectors in a composite radiation shield and separating the detectors with a separator that absorbs X-rays, and quantifying the presence of the CGX emitter in the sample. This method can detect an amount of CGX emitter in the sample of less than 100 picoCurie.

The EC isotopes that are preferred according to the invention are the CGX emitters of Lists 1–4, with those having half-lives between five hours and one year most preferred.

---

LIST 1: SELECTED LIGHTER EC ISOTOPES

---

$Be^7$ (53.6 d)
$Na^{22}$ (2.58 y)
$Ar^{37}$ (34.3 d)
$C^{49}$ (330.0 d)
$Cr^{48}$ (23.0 h); $Cr^{51}$ (27.8 d)
$Mn^{52}$ (5.6 d); $Mn^{54}$ (291.0 d)
$Fe^{52}$ (8.0 h); $Fe^{55}$ (2.7 y)
$Co^{55}$ (18.0 h); $Co^{56}$ (77.3 d); $Co^{57}$ (270.0 d); $Co^{58}$ (71.0 d)
$Ni^{56}$ (6.4 d); $Ni^{57}$ (1.5 d)
$Cu^{64}$ (12.8 h)
$Zn^{62}$ (9.3 h); $Zn^{65}$ (245.0 d)
$Ga^{66}$ (9.5 h); $Ga^{67}$ (78.0 h)
$As^{71}$ (62.0 h); $As^{72}$ (26.0 h); $As^{73}$ (76.0 d); $As^{74}$ (18.0 d)
$Se^{72}$ (8.4 d); $Se^{75}$ (120.0 d)
$Br^{76}$ (16.5 h); $Br^{77}$ (2.6 d)
$Kr^{76}$ (10.0 h); $Kr79$ (1.6 d)
$Rb^{82m}$ (6.3 h); $Rb^{83}$ (83.0 d); $Rb^{84}$ (33.0 d)
$Sr^{82}$ (25.5 d); $Sr^{83}$ (1.6 d); $Sr^{85}$ (64.0 d)
$Y^{83}$ (108.0 d); $Y^{86}$ (14.6 h); $Y^{81}$ (3.33 d)
$Zr^{88}$ (85.0 d); $Zr^{89}$ (3.29 d)
$Nb^{92}$ (10.1 d)
$Tc^{93m}$ (60. d); $Tc^{96}$ (4.3 d); $Tc^{99m}$ (6.0 h)
$Ru^{97}$ (2.9 d);
$Rh^{99}$ (16. d); $Rh^{100}$ (21. h); $Rh^{102}$ (206 d)
$Pd^{100}$ (4.0 d); $Pd^{101}$ (8.5 h); $Pd^{101}$ (17 d)
$Ag^{105}$ (40 d); $Ag^{106m}$ (8.3 d); $Ag^{108m}$ (>5 y)
$Cd^{107}$ (6.7 h); $Cd^{109}$ (470 d)
$In^{111}$ (2.81 d); $In^{113}$ (118 d)
$Sn^{113}$ (118 d)
$Sb^{119}$ (158 d); $Sb^{122}$ (2.8 d)
$Te^{118}$ (60 d); $Te^{119}$ (45 d); $Te^{121}$ (17 d)
$I^{123}$ (4.2 d); $I^{125}$ (60 d); $I^{126}$ (13.2 d)
$Cs^{132}$ (6.5 d)
$Ba^{128}$ (2.4 d); $Ba^{131}$ (11.6 d)
Subtotal 71 isotopes

---

LIST 2: EC ISOTOPES OF LANTHANIDES

---

$La^{135}$ (19.8 h)
$Ce^{133}$ (6.3 h); $Ce^{134}$ (3.0 d); $Ce^{135}$ (22.0 h); $Ce^{137}$ (9.0 h); $Ce^{139}$ (140 d)
$Nd^{140}$ (3.3 d)
$Pm^{143}$ (265 d); $Pm^{144}$ (440 d); $Pm^{145}$ (18 y); $Pm^{46}$ (710 d); $Pm^{158m}$ (40.6 d)
$Sm^{145}$ (340 d)
$Eu^{145}$ (5.6 d); $Eu^{146m}$ (1.58 d); $Eu^{146}$ (4.6 d); $Eu^{147}$ (24 d); $Eu^{148}$ (54 d); $Eu^{149}$ (120 d); $Eu^{150}$ (14 h); $Eu^{150}$ (5 y); $Eu^{152}$ (13 y)
$Gd^{146}$ (48 d); $Gd^{147}$ (35 h); $Gd^{149}$ (9 d); $Gd^{151}$ (120 d); $Gd^{153}$ (200 d)
$Tb^{151}$ (19 h); $Tb^{152}$ (18 h); $Tb^{153}$ (2.58 d); $Tb^{154m}$ (8 h); $Tb^{154}$ (21 h); $Tb^{165}$ (5.4 d); $Tb^{160}$ (73 d)
$Dy^{155}$ (10 h); $Dy^{157}$ (8.2 h)
$Tm^{165}$ (1.21 d); $Tm^{167}$ (9.6 d); $Tm^{168}$ (85 d)
$Yb^{169}$ (32 d)
$Lu^{169}$ (1.5 d); $Lu^{170}$ (2.0 d); $Lu^{171}$ (8.3 d); $Lu^{172}$ (6.7 d) $Lu^{173}$ (1.3 y); $Lu^{174}$ (165 d)
$Hf^{173}$ (24 h); $Hf^{175}$ (70 d)
$Ta^{175}$ (11 h); $Ta^{176}$ (8.0 h); $Ta^{177}$ (2.21 d); $Ta^{179}$ (1.6 y); $Ta^{180m}$ (8.1 h)
Subtotal Lanthanides: 54 isotopes

---

LIST 3: EC ISOTOPES OF VERY HEAVY METALS

---

$W^{181}$ (130 d)
$Re^{181}$ (20 h); $Re^{182m}$ (13 h); $Re^{182}$ (64 h); $Re^{183}$ (71 d); $Re^{184m}$ (2.2 d); $Re^{184}$ (50 d); $Re^{186}$ (90 h)
$Os^{183m}$ (10 h); $Os^{183}$ (12 h); $Os^{185}$ (94 d)
$Ir^{185}$ (15 h); $Ir^{187}$ (12 h); $Ir^{111}$ (1.71 d); $Ir^{189}$ (11 d); $Ir^{190}$ (11 d)
$Ir^{192}$ (74 d)
$Pt^{191}$ (3.0 d)
$Au^{193}$ (15.8 h); $Au^{194}$ (39 h); $Au^{195}$ (200 d); $Au^{196}$ (5.55 d)
$Hg^{193m}$ (1.1 d); $Hg^{193}$ (6 h); $Hg^{194}$ (130 d); $Hg^{195}$ (1.66 d); $Hg^{195}$ (9.5 h); $Hg^{197m}$ (24 h); $Hg^{197}$ (2.71 d)
$Tl^{200}$ (1.08 d); $Tl^{201}$ (3.04 d); $Tl^{202}$ (12 d); $Tl^{204}$ (3.9 y)
$Pb^{200}$ (21 h); $Pb^{201}$ (9.4 h); $Pb^{202}$ (2.17 d)
$Bi^{203}$ (12.3 h); $Bi^{204}$ (11.6 h); $Bi^{206m}$ (15.3 d); $Bi^{206}$ (6.3 d); $Bi^{207}$ (30 y)
Subtotal heavy metals: 40 isotopes

---

LIST 4: EC ISOTOPES OF ACTINIDES

---

$Po^{206}$ (8.8 d)
$At^{210}$ (8.3 h); $At^{211}$ (7.2 h)
$Rn^{211}$ (16 h)
$Ac^{226}$ (29 h)
$Pa^{228}$ (22 h); $Pa^{229}$ (1.5 d)
$U^{231}$ (4.2 d)
$Np^{234}$ (4.4 d)
$Pu^{234}$ (9 h); $Pu^{237}$ (45.6 d)
$Am^{239}$ (12 h)
$Cm^{241}$ (35 d)
$Bk^{245}$ (4.95 d); $Bk^{246}$ (1.8 d)
Subtotal Actinides: 15 isotopes Preferably, the CGX emitter is an isotope of an element that forms covalent bonds, or one that can be chelated to an organic compound. Preferably the isotope is $I^{123}$, $I^{125}$, $I^{126}$, $Br^{76}$, or $Br^{77}$, and most preferably $I^{125}$. Preferably the CGX emitter is an isotope of the family of CGX lanthanide isotopes.

The CGX emitter may be coupled to an organic molecule, such as an organic precursor for the synthesis of a macromolecule, a steroid compound (e.g. estrogen), a protein, or a precursor of nucleic acids, biologically or synthetically produced.

The CGX emitter may be incorporated in a primer for nucleic chain elongation, and used in an in vitro nucleic acid amplification protocol, or in the polymerase chain reaction (PCR) process, wherein the polymerase chain reaction can be stopped while the amplification is still exponential, after less than ten amplification cycles. The primer may also be used in a linear polymerase reaction.

The CGX emitter may also be coupled to a monoclonal or polyclonal antibody or an antigen, and the antibody or antigen can be used in a competitive assay. For example, an antibody can be used to detect cancerous cells in a physiological sample. The level of estrogen and other steroids may be used to diagnose breast cancer.

The CGX emitter may be coupled to a unicellular organism such as a virus, a bacterial cell, an algae cell, a fungal cell, or a protozoa. The virus may be an agent of sexually or blood transfusion transmitted disease, and the bacteria may be tubercular bacillus or bacteria which are precursors of sexually transmitted diseases.

The competitive assay may be used to detect contamination of human physiological fluids such as blood, urine, sputum, tear drops, sweat, amniotic fluid or spinal fluid, or animal physiological fluids.

The competitive assay may be used to detect contamination of food and agricultural products, such as the presence of microorganisms and their toxic byproducts, e.g. aflatoxins or mycotoxins. The competitive assay may also be used to detect contamination of samples of water, soil or air from the environment, and chemical contamination such as pesticides, herbicides, PCBs, dioxin, and heavy metals.

The competitive assay can be performed upon airborne substances in a clean room environment, and data are used to estimate the number and size distribution of micron sized dust and other particulates suspended in the air.

At least one of the detectors is preferably a Ge-semiconducting detector optimized for detection of X-rays, preferably less than 0.5 inch thick and using a cryostat with thin beryllium or aluminum windows. In an alternative embodiment, at least one of the detectors is a spatially resolving gas detector, preferably a thin self-limiting streamer chamber, and the spatial resolution is obtained by imaging, using a CCD camera.

At least one of the detectors preferably comprises a scintillator, preferably an inorganic scintillator with good energy resolution, and a photosensor, with the scintillator being an appropriately doped NaI or $CaF_2$ crystal with a thickness less than 0.5 inch, and using a photomultiplier to amplify the signal from the scintillator. A large surface photodiode avalanche photodiode or photomultiplier is preferably used to amplify the signal from the scintillator. A low radioactive background quartz window can be placed between the scintillator and photosensor.

Preferably, the detector is shielded in a low radioactive background housing covering the surface of the scintillator, of less than about 0.1 g/cm² in thickness and made of low atomic number elements (Z less than 10) having low radioactive background. The housing preferably comprises beryllium, aluminum, or plastic. Preferably, the detector is shielded within a shield comprising a very high atomic number metal (Z>61), such as lead, tungsten, or mercury. Most preferably, the detector is shielded within a shield comprising subsequent layers of materials with low atomic number (Z less than 20), medium atomic number (Z between 21 and 60), and high atomic number (Z greater than 61), with the high atomic number layer being the most external, wherein the materials with low and medium atomic number are highly purified copper (Cu) and tin (Sn), respectively.

Preferably, the majority of X-rays are absorbed by placing a separator between the separate radiation detectors. The separator preferably comprises a layer of a high atomic number material (Z>61) with a thickness larger than 2 mm. The separator may be cladded on both surfaces with thin layers of materials with low atomic number and medium atomic number. The low and medium atomic number materials can be highly purified copper (Cu) and tin (Sn), respectively.

There is preferably a conical hole in the separator, and the sample is placed in the hole. The sample may be placed in a sample holder comprising a narrow microcapillary ended with a spherical, hollow tip containing up to 0.1 cc of liquid, and then placed in the separator. The sample holder may consist essentially of material with both very low atomic number (Z less than about 10) and low radioactive background, such as beryllium, aluminum, or plastic.

The separator may have a plurality of conical holes ordered into an easily distinguished pattern, and samples to be studied can be placed into the holes. The samples may be blotted upon an appropriate thin film with patterns substantially identical to the hole pattern in the separator, and the blotted film aligned with the separator between the detectors. The separator may consist of two parts, each with identical hole patterns, and the blotted film can be placed between these two parts.

The method may further comprise amplifying the pulse from the scintillator with low noise preamplifiers, shaping the pulse into a characteristic triangular pulse with rise time shorter than 200 nsec and fall time between 0.5 and 5 microseconds, and matching the pulse shapes and amplitudes in both crystals to better than 10%. The preamplifiers are preferably two stage preamplifiers.

The method preferably comprises analyzing each pulse for amplitude by appropriate single channel analyzers (SCA), and using the SCA outputs in a coincidence circuit (COINC) with a well defined time window, further comprising analyzing the shape of each pulse in an analog-to-digital converter (ADC) or digital storage oscilloscope (DSO) sampling at a rate of at least 10 MHz per channel, using the signal from the coincidence circuit as trigger.

The method preferably comprises storing pulse shape records from the ADC or DSO in the fast memory of a computer for further data analysis, analyzing each pulse shape record by at least one software module having acceptance criteria, rejecting a pulse on-line if it does not satisfy the acceptance criteria of all the software modules, and counting the pulse if it satisfies the acceptance criteria of all the software modules.

The software modules preferably include:

a) analyzer of pulse amplitude;

b) analyzer of the total pulse width;

c) analyzer of the shape of the rising part of the pulse;

d) analyzer of the shape of the falling part of the pulse;

e) analyzer of the delay between the pulses from the two detectors;

f) analyzer of pulse multiplicity;

g) analyzer of the pre-pulse trace; and h) comparator of the pulse shape with a standard high energy photon pulse shape using a least squares technique;

individually or in combination.

Coincident pulses may be selected to build a three dimensional scatter plot matrix, using the matrix to further optimize background rejection in off-line mode. Preferably, the invention comprises coupling at least one of the scintillators with a spatially resolving photomultiplier tube, amplifying the output pulses from the photomultiplier tubes by at least two matched low noise amplifiers, and using the outputs as inputs to multichannel analog-to-digital converters or digital storage oscilloscope modules. Four matched low noise amplifiers are preferably used.

The method may further comprise analytically comparing the amplified pulses from the spatially resolving photomultiplier tube with standard shape pulses, and using only events satisfying the standard shape condition in at least two and preferably all four photomultiplier tube outputs are used to build 1D or 2D images.

At least one of the detectors may be a phoswitch module comprising a gamma detector consisting of two optically coupled scintillators with different characteristic response times. The phoswitch preferably comprises a very thin scintillator with high energy resolution, closer to the sample, and a thick, high stopping power scintillator, and the two scintillators are separated by a few millimeters of optically transparent material with low radioactive background. Preferably, the scintillator with high energy resolution comprises NaI(Tl) or CaF2(Eu), the thick, high stopping power scintillator comprises CsI or BGO, and the optically transparent material comprises acrylic plastic or quartz. The signal from the phoswitch is preferably amplified by a fast, low noise shaping amplifier and then analyzed by data analysis modules as described above, and the pulse shape analysis is then used to localize the scintillator element inside the phoswitch within which the photon is absorbed.

BRIEF DESCRIPTION OF THE DRAWINGS

The invention is better understood by reading the following detailed description with reference to the accompanying figures, in which.

DETAILED DESCRIPTION OF THE PREFERRED EMBODIMENTS

In describing preferred embodiments of the invention, specific terminology is employed for the sake of clarity. However, the invention is not intended to be limited to the specific terminology so selected, and it is to be understood that each specific element includes all equivalents which operate in a similar manner to accomplish a similar purpose.

The invention relates to a new class of devices used for quantitation of a specific class of radioisotopes. They have the following advantages over the prior-art detectors:

increased sensitivity, i.e. sub-pico Curie samples can be measured;
 multicolor, i.e. plurality of isotopes can be measured and distinguished in the same sample;
 multisample, i.e. the same device can measure many separate samples;
 portability.

Not only are these devices very sensitive, i.e. they permit detection of $5*10^{-21}$ mole of labeled molecules, but they also yield very reproducible results. Ten independent measurements of attomole samples show the same result with excellent reproducibility of better than 1%. Furthermore, we have documented excellent linearity of our device; better than 1% over six orders of magnitude. The features of the disclosed coincident gamma/x-ray detectors (CGXD) lead to important applications in a plurality of fields, including biomedical and environmental applications.

The wide range of applications of this technique includes such fast-developing fields of medicine and biochemistry as immunoassay, DNA sequencing, chromatography, and medical imaging. In addition, these techniques can be extended to such fields as pollution monitoring, waste management, the chemical industry, forensics, and more. More specifically, these technique will find important applications in:

molecular biology;
 biomedical diagnostics;
 environmental pollution detection;
 materials fabrication;
 petrochemical industry.

This invention relates to improvements in the art of quantitating members of a rare family of photon-emitting radioisotopes. The relevant atomic and nuclear physics is first summarized. There are about a thousand gamma emitting isotopes. About a hundred of these acquire their excited nuclear state through an electron capture (EC) from the S shell (lowest energy state). An unstable S shell vacancy and an unstable excited nuclear state result. Within less than a microsecond, gamma photon emission from the nucleus may occur (prompt emission), or the nuclear excitation may have a much longer half-life (delayed emission). The probability of each of the various decay channels is highly isotope-dependent, and the controlling physics is very complicated. The S shell vacancy may be filled by the dropping of an outer shell electron with concomitant emission of an X-ray photon or through a cascade of low energy transitions (typically below 10 keV) which progressively restructures the electron shells. The EC decays with prompt gamma and X-ray emission are of highest utility for the disclosures herein and are hereafter referred to as proceeding through the "GX" channel. In the following, members of this subclass of EC isotopes are referred to as Coincident Gamma/X-ray isotopes (CGX isotopes).

For most applications only EC isotopes with lifetimes of a few hours to a few years are of importance, and half lives with a lifetime longer than a few days are preferred. List 1 illustrates the properties of some of these EC isotopes. The EC isotope $I^{125}$ in particular is involved in some applications described below. According to results obtained with older instrumentation and recorded in nuclear data tables, coincident emission of a 35 keV nuclear gamma and one of several possible X-rays in the 27–31 keV range occurs in 7% of the $I^{125}$ decays. With the improved system herein disclosed, experiments in actuality revealed a coincidence in 25–35% of the decays.

The CGX isotopes are chemically diverse, including the noble gas $Ar^{37}$. Several of the CGX, radioisotopes form covalent bonds. Many are multivalent metals. Radioisotopes forming covalent bonds have been utilized for years in organic and biochemical analyses. In recent years multivalent metals have also entered service as labels. They are captured in chelating complexes which are constituents of, or can be adducted to, molecules or macromolecules to be quantitated. In addition the metal scavenging protein metallothionine can capture 20–40 atoms of multivalent metals. Metallothionine has recently been used as a constituent of genetically engineered fusion proteins. Its high carrying capacity is thus coupled, for example, with the targeting specificity of antibodies. A highly selective delivery of label to particular antigenic targets within complex cellular mixtures can thus be achieved. Thus, the CGX isotopes can be used in a variety of prior art labeling strategies. Labeling processes per se are not subject of this invention.

The extension of radioisotope counting into very low activity domains by the application of CGX isotopes and selective quantitation of CGX events are the primary subjects of this invention. To quantitate CGX events with maximal sensitivity, the various sources of background were aggressively explored. Some of the findings violated expectations based on experiences with prior-art systems. As background sources were recognized, there was a progressive implementation of countermeasures. The resultant instrument can function in either single photon or selective CGX counting modes and is referred to as a Coincident Gammafix-ray Detector (CGXD). By itself, hardware implemented coincidence counting is not novel. However, using the coincident photons originating from distinct nuclear and electron shell excitations to achieve background rejection is non-obvious and is novel. Other novel features were synergistically combined with coincidence detection during the development program. Together they led to construction of a low cost system allowing quantitation of CGX sources with activities too low to be discriminated above the background registered by traditional single gamma counters.

Prior-art instruments counting single gammas have been built for broad applicability to permit measurements of large families of gamma emitters with energies ranging from a few tens of keV to a few MeV. In these devices, multichannel analyzer (MCA) electronic systems distinguishing energy pulse heights generally serve to discriminate the energies of emissions for the plurality of source isotopes. For any isotope, a maximum counting efficiency is commonly desirable to provide highest sample throughput.

In contrast, the special CGXD capabilities are relevant to only the EC isotopes, which are a small sub-group of the much larger family of gamma emitting isotopes. And even for the EC isotopes, the CGX channel is relatively rare, which eliminates use of many isotopes currently used. Furthermore, in the selective CGX counting mode, detection efficiency is always less than that of single gamma counters. Until our invention, the lower detection efficiency was believed to decrease the measurement throughput, and only highly efficient detectors have been used in prior-art devices. Thus, the utility of a CGXD is highly non-obvious.

We proved, however, that CGXD greatly extends the useful activity range of isotope quantitation. General usages of $I^{125}$ provide examples. Iodine is readily adducted at double covalent bonds of organic molecules, including nucleic acids, carbohydrates and proteins. Iodine labels are extensively employed in basic research in biochemistry, nuclear medicine and molecular and cellular biology. They dominate broad families of immunoassays utilized in clinical medicine. The prior-art detectors have radioactive backgrounds in the 10–40 counts per minute (cpm) range, which leads to the need to use isotopes with relatively large activity. About ten nanoCuries (nCi) of isotope per sample is typically needed for assays using single photon quantitation, in order to provide statistical significance above the background. With the CGXD optimized for rejection of events lacking the $I^{125}$ coincident CGX signature, the background uncertainty is only one count per day (1 cpd). Consequently, a picoCurie (pCi) input of $I^{125}$ will suffice for each sample in a typical assay protocol. In contrast with prior-art detectors a thousand fold smaller amount of radioactivity is needed. Actually, these pCi activities are much below the ambient radioactivity.

The direct application of the above said methods is for quantitation using ultralow radioactivity labels. Their main application is in biomedical diagnostics. These applications include DNA sequencing, DNA fingerprinting and diverse forms of competitive and/or binding assays, e.g. radioimmunoassay (RIA). Typically a plurality of dilutions is measured to provide a diagnostically meaningful result. Competitive radioassays have many advantages (very high sensitivity, large number of well-understood/calibrated kits, and generally years of accumulated know-how) and are widely used in biomedical applications. However, RIA is increasingly being replaced by the techniques of fluoroimmunoassay (FIA) and enzymatic immunoassay (EIA). The main reason is that the activity of the used radioactive markers is around a microCurie per assay, which creates significant hazardous material handling and disposal problems. With implementation of selective CGX counting, higher sensitivity, reductions in isotope acquisition costs, smaller exposure of personnel and diminished radioactive waste disposal are feasible. If pCi isotope inputs are implemented, exposure to toxins and pathogens which may be resident in assay samples or reagents are a far greater safety concern than the minute amount of $I^{125}$ used.

When desirable, sample counting can first proceed without coincidence for samples with activity significantly above the single gamma background. Subsequently, samples of lower activity can be recounted in the coincidence mode to achieve valid quantitation with extreme background rejection. Using the pro-established frequency of the CGX channel for the particular EC isotope, the results of the two counting modes can be computationally combined. With a dynamic range about 1000-fold greater than single gamma counters, differential treatment of samples with low and high amounts of target materials will not be necessary. This will decrease assay costs and increase their reliability.

The advantage of the higher sensitivity of CGXD can be illustrated on a particular example of an important application area, which is the analysis of polymerase chain reaction (PCR) products. In PCR reactions, pre-existing knowledge of nucleic acid sequence is utilized to ascertain whether a target sequence is resident in a complex nucleic acid mixture, for example, a single HIV virus in a population of human cells. A cyclic replication reaction selectively amplifies the target sequence, until the amplified nucleic acids can be quantitated by some end point analytical technique. A practical problem is that artifactual products are unavoidably generated. Some of these artifacts are amplified faster than the target sequence. The more amplification cycles are necessary, the greater the probability the sought target signal will be swamped. Thus, minimizing the number of PCR cycles increases the signal/noise ratio of target/artifact nucleic acids. The PCR reaction is compatible with CGX labeling. For example the primers for each reaction cycle could carry $I^{125}$ labels. Many fewer amplification cycles, with concomitant limitation in PCR artifact accumulation, would then suffice when CGXD methodology is used in the endpoint quantitation. These same advantages can be conferred to a number of other amplification strategies which are becoming competitive with PCR.

The CGXD retains the capacity of simpler MCA (multichannel analyzer) based single gamma counters to discriminate co-resident isotopes when the known gamma energies of the sources are distinguishable. In addition, the separate characterization of the X-ray provides a further criteria for discriminating source isotopes in mixtures. Thus the CGXD supports the simultaneous quantitation of more complex isotopic mixtures than simpler counters. Only menu driven changes in the software described below are needed to select for the known isotopes in a mixture. For brevity, this simultaneous quantitation capacity will be hereafter referred to as "multicolor" capacity.

Radiation detectors with imaging capacities are available. The ancient prototype is X-ray film which unfortunately cannot be used in CGXD. Spatially resolving detectors are relevant to CGXD capabilities only if they report the arrival time of radiation and thereby support background suppression by coincidence counting. These now include spatially resolving semiconducting detectors and spatially resolving gas detectors. One can also use scintillators with appropriately coupled spatially resolving photon detectors, e.g. imaging photomultiplier tubes (PMTs) and CCDs. For example, imaging PMTs are designed to locate absorption sites on a single planar scintillator by providing the output of four channels within a single PMT. The burst of low energy photons resulting from stoppage of an energetic particle in the scintillator is distributed among the separate parts of the PMT. The appropriately analyzed outputs of the four channels provides for location of the absorption site on the scintillator. The quantitative imaging of a two-dimensional (2D) isotope source is thus supported. A regular array of samples spotted on a thin support membrane can represent hundreds of assay samples to be simultaneously quantitated. Imaging PMTs are compatible with the selective CGX counting strategy as further described below. Thus a low count rate of individual, low activity CGX samples can be compensated for by quantitating numerous samples in parallel. Even higher spatial resolution can be achieved when CCDs are coupled to the scintillator.

A spatially resolving CGXD can be used where autoradiography has traditionally been employed, with the added advantage of multicolor capability. With prior art label detection techniques such as chemiluminescence or conventional autoradiography, any superimposed target distributions must be read out through sequential interrogation cycles. In many applications, the 2D target pattern is transferred to a durable membrane, producing a tough 2D blotted representative of the original 2D specimen, the blot. In other protocols, dot blots are produced by spotting nucleic acid or protein samples onto a membrane, and stably fixing them thereupon. Commonly, different analytical reagents must be used to display/quantitate various targets of a 2D pattern. Sequential interrogations are employed. This process is tedious and the frequent handling of the specimen or its blot membrane image limits its usable life span. With CGXD probes for the distinct targets can carry distinguishing labels. The co-resident target distributions can thus be measured individually but simultaneously. When the 2D specimen holds antigens (Ag), several antibodies (Ab) with distinguishing CGX labels could be separately prepared and then pooled for simultaneous interrogation of the blot. Conversely, antibodies could be bound on the 2D specimen and the positions displayed with a number of antigens carrying distinguishing CGX labels. These two formats together support a variety of immunoassays.

When the 2D specimen has bound nucleic acids (DNA or RNA), nucleic acid probes complementary to particular target sequences can be separately CGX labeled and then pooled for simultaneous interrogation. These formats will support protocols of sequencing by hybridization (SBH) with short oligomer probes, and both multiplex sequencing and genomic sequencing in which multiple fractionated products of DNA sequencing reactions are superimposed.

The sensitivity of these immunological techniques will be further enhanced by the use of CGXD, which can reach sensitivity levels previously achieved only with more difficult techniques such as PCR. This extra sensitivity will be very useful in certain biomedical applications wherein a sensitivity to a few hundred molecules is being searched for. These applications include searches for the most potent toxins and some microorganisms. The sensitivity of CGXD may permit direct detection of a single virus or bacterium in a few milliliters of physiological fluid. It can considerably facilitate the detection of metastasis of diverse cancers, e.g. breast cancer. The improved sensitivity to toxins, e.g. aflatoxins and mycotoxins, will permit better quality monitoring during food processing, including storage of grains and other agricultural products.

There is a new family of applications made possible by the ultralow background capabilities. The deliberate introduction of radioisotopes or ionizing radiation into the human body is considered hazardous. It is performed for tumor destruction, or when the value of diagnostic information obtained from the radiation is considered to far outweigh the dangers of the radiation itself. The human body is not, however, a radiation free environment. In physiological fluids, $K^{40}$ is the predominant source of radiation. There is in addition absorbed radon gas and its decay daughters, penetrating cosmic rays and traces of heavy radioactive elements. With the CGXD, selected EC isotopes can be accurately quantitated at such low activities that they do not constitute a significant increment to the "natural" burden of ionizing events. Thus CGX labeled compounds can be used without fear of inducing damage above the "spontaneous" background. This opens a whole family of diagnostics for routine use, which could before only be justified for use with severely compromised patients.

There are related environmental applications. CGX isotopes or CGX labeled compounds could be released in the external environment as tracers, when the added radioactivity is far less than of the "natural" sources. For a particular example, the CGX tracers could be added to containers or piping to assess leakage. The unreactive noble gas $Ar^{37}$ would be ideal for this purpose. Chemical tank farms, railway and highway tank cars and production plants with toxic chemicals are obvious markets. Other soluble tracers could be used where the surrounding ground/waters have already been so badly contaminated that the continuing slow leaks from tanks or pipelines are difficult to locate. The family of CGX isotopes includes several relatively short lived isotopes, so that even its small added radiation burden would very quickly disappear from the environment.

Tracer techniques are not relevant when the goal is to quantitatively measure the distribution of target substances in the environment, such as toxins or residual pesticides on crops. The targets are not initially labeled but their quantitation can be achieved through immunoassay techniques. Greatest sensitivity is achieved by radioimmune assays, commonly using $I^{125}$ as a label on either antibody or antigen reagents. The CGX labeling of reagents and CGXD readout will extend the sensitivity of such assays, where they have in the past been limited by the radiation background. Antibodies have now been raised against many carcinogens, herbicides and pesticides. The homogenous monoclonal antibodies produced from hybridomas (basically clones of immortalized lymphocytes producing the desired single antibody) are the reagents of choice.

In environmental diagnostics, thousands of samples are studied to assess whether or not the contamination by a given pollutant is above the permissible level. These levels are typically around a picomole/ml, i.e. about three orders of magnitude higher than the limit of sensitivity of good immunoassays. Thus, one can pool hundreds of samples together and by testing the resulting "cocktail" check if any of the samples is contaminated. In the rare cases of cocktails showing positive, the statistical techniques based on "Boltzano division" permits one to define which samples are actually contaminated in a relatively small number of steps. Thus, instead of measuring thousands of samples, typically a few dozen appropriate cocktails are measured, diminishing the cost by a factor of at least twenty. This technique is reliable only if the sensitivity of the assay is a factor of a thousand greater than the permissible contamination levels. The superior sensitivity of the CGXD supports this methodology.

In natural environments, local patterns of water flow and soil inhomogeneities can lead to concentrations of contaminants in a few "hot spots" which are often only a few meters in diameter. Thus the dynamical range of the contamination levels is as high as a few thousand. On the other hand, within a square kilometer very few hot spots may exist, resulting in only one per thousand or fewer samples testing positive for the contamination. Current techniques, especially mass spectroscopy (MS) and high performance liquid chromatography (HPLC), test one sample at a time. The compatibility of CGX isotopes with 2D imaging permits measurement of hundreds of samples concurrently while maintaining extreme background rejection and hence the required high dynamic range.

The innovative blend of the superior sensitivity of the CGXD technique and the specificity of competitive assay technology permits considerable improvements when used in "clean room" applications. The development of very high density VLSI chips requires increasing levels of purity in clean rooms used in semiconductor fabrication. The problem of defects due to contamination in the clean room environment is one of the crucial limits to high yields in the production of next generation chips. New diagnostic methods to assess the air/chemical purity have to be developed to achieve the goals of next generation semiconductor fabrication. The important point is that the majority of contaminants are biological in origin, e.g. parts of human skin, hairs, strands of material from clothing, bacteria, pollen etc. for which very specific monoclonal and polyclonal antibodies either already exist or can be developed. Preliminary estimates suggest that contamination by a few sub-micron sized particles per cubic meter can be detected. For example, when using a single monoclonal antibody, parts of human skin can be detected at $10^{-15}$ mole. The limitations are due to the specificity of currently used immunoassays. A number of typical contaminants should be quantitated in parallel, which leads to need for "multicolor" assays. We believe that the utility of immunoassays in clean room diagnostics can be considerably improved by using a plurality of monoclonal antibodies concurrently. This requires an analytical technique which is able to quantitate coincident multi-tags and perform the tests with high throughput; CGXD excels in these respects.

COMPARISON WITH PRIOR-ART X-RAY AND GAMMA DETECTORS

In the following description of prior-art detectors it is appropriate to classify the existing radiation detectors into:

a) ultralow background detectors with radioactive background of less than 0.1 count per hour (<0.1 cph);

b) very low background detectors with radioactive background of less than 1 cph (<1 cph);

c) low background detectors with radioactive background less than 1 count per minute (<1 cpm).

In the last few years, there has been very fast development of ultralow radioactive background techniques (see reference 1). These developments have been spearheaded by a few large underground laboratories around the world using large (a few kilograms of mass), high purity Germanium (Ge) detectors. The radioactive background has been diminished by about five orders of magnitude in the last decade and is currently about one count per day at hard X-ray energies (20–50 keV). For radioisotopes with half-lives of a few hours to a few days, the detection of a solitary radioactive atom is now possible. These facilities, however, are very expensive; the typical cost of such systems is about $250,000. They are fully committed to fundamental physics research, and their remote, underground location is far beyond the reach of the common analytical laboratory.

The are worldwide only a few very low radioactive background detectors placed on the Earth's surface. They feature Ge-detectors and a very heavy, typically over a ton of lead, shield.

There arc commercially produced low background systems for more general research and biomedical and environmental diagnostic applications. In these top-of-the-line detectors a radioactive background of about ten counts per hour has been achieved. They are based predominantly on semiconducting Ge detectors, typically with scintillator anti-coincidence shield. Currently, the Ge-spectrometers are the most sophisticated and best performing gamma detectors. Their main advantage is their excellent energy resolution, dE/E<1%, for both hard X-rays and gamma photons. They are often operated with anticoincident active shields. However, the Ge detectors have to be operated in liquid nitrogen, which severely limits their usefulness in commonplace biomedical and environmental diagnostics, particularly when portability is desired. Another disadvantage is their high price, which is about $30,000 per unit for the least expensive devices. For detectors of higher energy gammas, 2 kg Ge detectors are required, with prices around $100,000.

The bulk of commercially available radiation detectors are characterized by radioactive background larger than one count per minute. These are most often gas detectors or scintillation detectors. Historically, gas detectors were first used in diagnostics. They are simple and reliable. Their energy resolution is typically 10% for hard-X-rays, Say at 30 keV. X-ray gas detectors with heavy passive shields typically have 20–30 cpm background. Because of their low stopping power and inconvenience due to the large size of gas purification systems, they have been replaced by scintillation counters. The important advantage of gas detectors in some applications is the availability of large size detectors with high spatial resolution. These are typically the multi-wire proportional chamber (MWPC) type detectors. The need for multichannel electronics leads to increase in cost. Furthermore, the radioactive background is proportional to the number of wires and can be quite elevated in MWPC gas detectors. Thus, the use of drift gas chambers featuring lower number of wires is preferred in ultralow background applications. However, for low energy deposition, e.g. when X-rays are stopped, it is difficult to built drift chambers with good spatial resolution in both directions.

Scintillation counting today is the most commonly employed method for isotope decay quantitation (see reference 2). Liquid or solid scintillatots are used to convert the beta or gamma decay energy into a pulse of visible photons, and the total photon number, which is proportional to the original particle energy, is analyzed. The scintillation detector systems for these applications were first developed in the 1960s, and only moderate improvements have been incorporated into today's commercial instruments. Their limitations are: weight and bulk due to necessary shielding; mediocre energy resolution which limits the number of co-resident labels that can distinguished; and background levels of the order of twenty counts per minute (20 cpm). Another practical consideration is that some scintillatots, e.g. NaI(Tl), are highly hydroscopic and thus require an appropriate housing.

Typically, a well scintillation detector ( a single crystal with a hole for a sample) is used to detect and quantify low energy gamma/X-ray emitting isotopes. To maximize the detection efficiency (DE) for higher energies, it usually has a rather large volume with typical energy resolutions of dE/E(FWHM) of 30% and 9% at 30 keV and 511 keV, respectively. Even with thick (3–4 inches of lead) shielding, the background count rate at low energies is of the order of 20–40 of counts per minute. The background is produced by cosmic rays entering the large detector volume, ambient radiation and internal contamination of the detector. The cosmic rays produce low-energy background counts in two major ways: through direct excitation of atoms in the detector which then emit characteristic X-rays, and by saturating the electronics which produces spurious pulses. High-energy gamma photons from the environment (mostly $K^{40}$, $Tl^{208}$, $Bi^{204}$, a radon daughter in the air, and man-made contaminants) penetrate through the shielding and produce secondary low-energy gamma/Xrays. Even with their high detection efficiency of 70–90%, the high background results in a minimum required input radioactivity of tens of nano-Curies per sample.

A recent advance in economical ultralow background counting is the Coincident Gamma Detector (CGD), which has been reduced to practice by the group of Dr. A. K. Drukier. The CGD is designed for detection and quantitation of isotopes which decay with the coincident emission of a positron and a gamma. Within 10 nanoseconds the positron annihilates with the electron producing two back-to-back gamma photons with energies of 11 keV. Events lacking this triple gamma signature are rejected. In U.S. Pat. No. 5,083,026 the Preferred Implementation of the CGD utilizes multiple scintillation detectors to register the three coincident high energy (E≧250 keV) gammas.

Recently, there has been a beneficial evolution of components which can be incorporated into CGX detection systems. Older generation scintillators are known to have radioactive contamination, e.g. ppm contamination with $K^{40}$ and ppb contamination with actinides. Thus, a large fraction of the radioactive background is from the crystals themselves. Ultrapure scintillatots have recently been developed for ultralow background searches for double beta decays and cold dark matter. They feature about three orders of magnitude lower radioactive background than previously available scintillators.

At this level, most of the background comes from $K^{40}$ in the glass of the PMTs. Quartz PMTs can be used but are quite expensive. Furthermore, even if the radioactive contamination due to $K^{40}$ is eliminated, there is a non-negligible radioactive background due to the photocathodes. In the past few years large area (larger than one $cm^2$) photodiodes (PDs) and avalanche photodiodes (APDs) have become commercially available. In contrast with PMTs, PDs/APDs are smaller, more robust physically, require only a low voltage power supply (typically <100 V for PDs) and have much lower total energy consumption. They are also less sensitive to temperature changes and stray magnetic fields. Thus, the replacement of PMTs with ultrapure Si-based devices is conducive to lower overall background and higher sensitivity.

Another possible detector used innovatively in CGXD is the phoswitch. It is a combination of two scintillatots with very different response times, both optically coupled to a single PMT or other photosensor. It allows for more efficient detection of low and high energy photons, say soft X-rays and gammas. One implementation is a thin NaI(Tl) crystal with a thick CsI crystal behind it, followed by the common PMT. For example a 0.1 inch NaI(Tl) scintillator serves as a high energy resolution, low energy gamma/X-ray detector in which hard gammas are rarely absorbed. The CsI scintillator serves as the hard gamma photon detector. Due to the different response times of the fast and slow scintillators, the pulse shape permits a determination of the scintillator in which a photon has stopped. The energy of the energetic photon can be calculated from the knowledge of the X-ray/gamma-ray absorption position and the pulse height. These capacities make the phoswitch useful for one of the CGXD implementations. It should be pointed out, however, that the prior-art phoswitch detectors used complicated hardware electronics to measure the scintillator light pulse duration. The prior-art implementations were appropriate for high energy gamma-rays, say E>200 keV and for high count rate experiments. When used for soft X-rays and in low count rate experiments the prior-art phoswitch detectors lead to artifacts.

There are also relevant developments in the use of compact computers and specialty electronics. IBM PC-compatible computers and light laptop/notebook versions with costs in. the $1000–$4000 range are now available. They or their "expansion" boxes can host digital storage oscilloscope (DSO) cards which can be simply plugged into an expansion slot. This provides the potential for pulse shape analysis of scintillation detector outputs as a tool for background rejection on a low cost computer platform.

Literature Cited

1. F. T. Avignone et al., Phys. Rev. C34 (1986) 666. R. L. Brodzinski et al., NIM A254 (1987) 472. R. L. Brodzinski et al., J. of Radioanalytical and Nuclear Chemistry, 124 (1988) 513.

2. Radiation Detectors, Harshow 1990.

3. U.S. Pat. No. 5,083,026.

EXAMPLE 1

The generic CGXD.

In principle, background rejection could be sought by utilizing the coincidence of gamma emission with low energy photons from electron shell cascades, in addition to X-rays. However the problems of background discrimination increase substantially for lower energy (UV, visible and even near infrared) photons and is much more severe than for X-rays. Thus for purposes of optimizing a system for counting CGX isotopes, e.g. $I^{125}$, the penalty of some loss of coincident events was accepted to achieve exceptional background rejection. $I^{125}$ emits a 35 keV gamma photon and in 25–35% of the decays there is coincidence between this gamma photon and one of a few characteristic X-ray photons with energies of 27 to 31 keV. The energy differences between the energy of the gamma and X-rays are small enough that a single thin scintillator/PMT system has a reasonable detection efficiency and energy resolution for both radiation types. For economic reasons scintillation counters with a few inch diameter NaI(Tl) crystals coupled to PMTs were used. Crystals with 2 inch and 3 inch diameters show similar performance. These high atomic number/high density inorganic scintillators feature superior stopping power, reasonable energy resolution, and the possibility of fast timing (<10 nsec.). The samples are placed between the faces of the opposed scintillators on a common axis. To optimize the detection efficiency the isotope samples are held on the center line between the faces of the minimally separated counters.

The analysis of the lists of appropriate CGX isotopes (see Isotope Lists 1–4) shows that NaI(Tl) detectors may permit recognition of up to 8 different gammas/X-rays in the useful energy range.

The effects of major background rejection measures which were progressively implemented during CGXD development are summarized in Table 1. Coincidence serves as the first background rejection measure. With MCA implemented coincidence, the background is reduced by about a factor of 100. This improvement alone provides better performance than the best prior-art commercial detector type: the germanium well detector with an active external shield. It should be remembered, however, that the use of coincidence leads also to a decrease in detection efficiency. With the two detector geometry and counters with 80% efficiency, the total probability of detecting coincident $I^{125}$ gamma and X-ray emission is about 15%. Thus, the CGX detector in which only coincidence is used has a signal/background ratio only a factor of a few better than prior-art detectors.

Passive shielding provides for some background rejection. Together with coincidence, an external composite shield reduced the background from 10 to 5 cph. The shield does not influence the detection efficiency but limits the detector portability. Typically, a composite shield consisting of layers of materials with high, medium and low atomic number is aborn a factor of two better than a simple, lead based shield. Optionally, the composite shield can be about a factor of two lighter than the equivalent lead shield.

To reduce "crosstalk" between the scintillation crystals, it is important to physically isolate them from each other as much as possible by using a gamma/X-ray absorbing material. Experiments with one counter and high activity $I^{125}$ sources established that a 1 mm lead foil is sufficient to absorb 99% of single photons. Surprisingly, the 1 mm foil was not adequate to optimally block the residual background when placed between two detectors. Rather, in the absence of a sample an increase of lead separator thickness to 3–5 mm was necessary before the decrease in background counts flattened. More complicated events than single photons are evidently being blocked by the thicker separator. For example, some events may be initiated by cosmic rays striking the separator plate, and scattering radiation into both crystals. Radioisotopic contamination of the lead may be another source which can shed/scatter coincident radiation into the opposed crystals. With the thicker separator plate, the probability of the multiple emissions reaching both detectors is diminished. When placed between the two scintillation crystals, the thick separator reduces the background by a further factor of four, down to about 1 cph, while decreasing the detection efficiency by no more than 10%.

Thick separators with a biconical hole whose solid angle just exposes the crystal faces have been developed which permits a compromise between shielding and detection efficiency requirements. A sample mount which allows optimal exposure of the crystals is both sample shape and size dependent. We developed a family of separators with variable hole size, which was shown experimentally to be important for samples of various volumes.

TABLE 1

Effects of radioactive background reduction factors.

| Coincident Gamma-ray/X-ray Detector With Opposed Detectors | | |
|---|---|---|
| 2 × NaI (Tl) | without coincidence | 40 cpm |
| 2 × NaI (Tl) | MCA implemented coincidence | 10 cph |
| 2 × NaI (Tl) | ibidem + thin composite shield | 5 cph |
| 2 × NaI (Tl) | ibidem + separator between scintillators | 1 cph |
| 2 × NaI (Tl) | ibidem + DSO pulse shape analysis | 1 cpd |
| Prior-art detectors with well crystal geometries: | | |
| NaI (Tl) | thin lead shield | 40 cpm |
| NaI (Tl) | composite passive shield | 20 cpm |
| NaI (Tll) | active shield [CsI] | 5 cpm |
| Ge | composite passive shield | 1 cpm |
| Ge | active shield [NaI (Tl)] | 20 cph | cpm = counts per minute
cph = counts per hour
cpd = counts per day

Both systematic and statistical uncertainties on the background measurements quoted in this Table are less than 5%.

Figure 1:
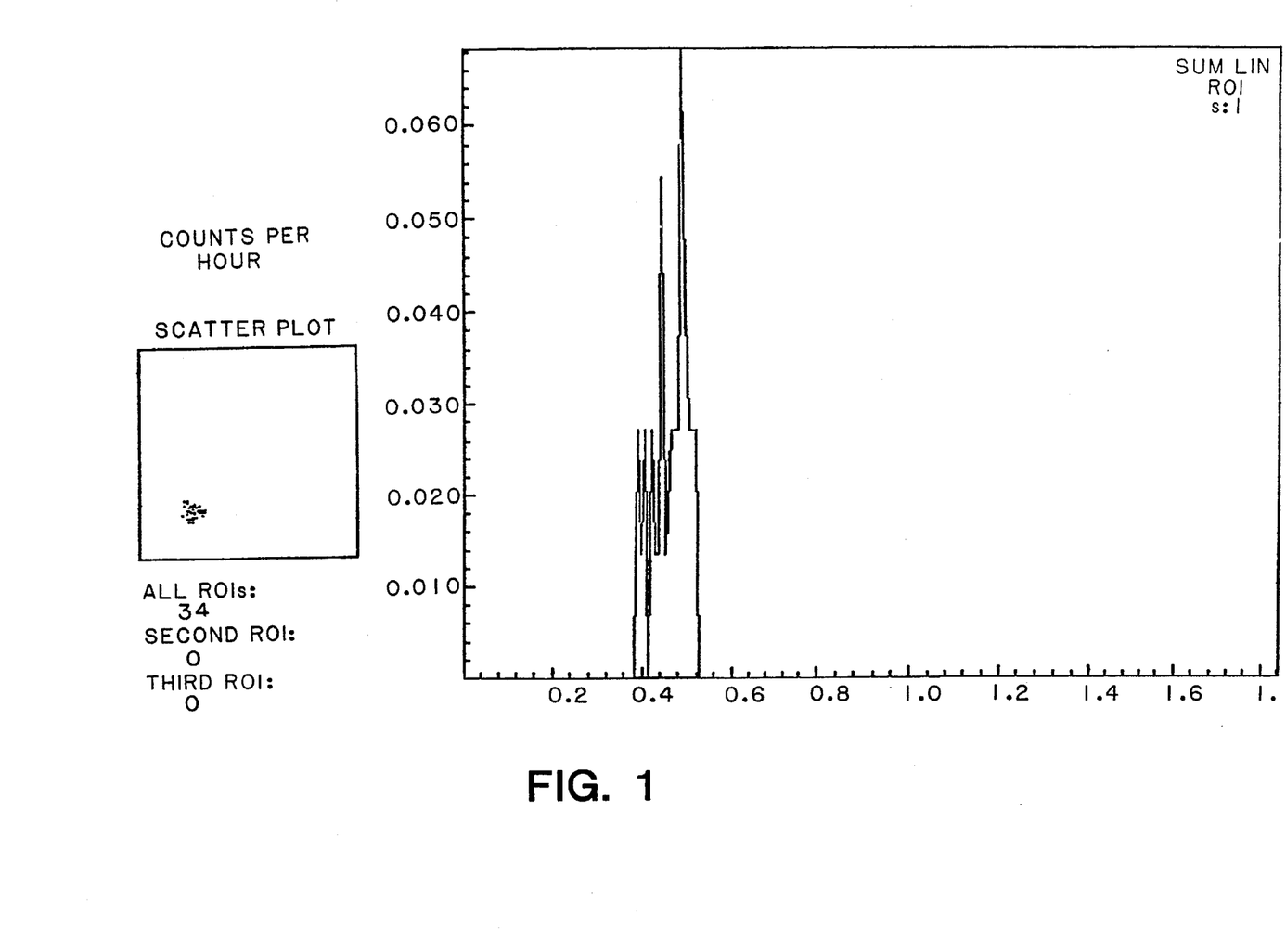
FIG. 1 illustrates the spectrum of picoCurie $I^{125}$ source obtained using a digital storage oscilloscope based spectrum analyzer, with an excellent signal to background ratio (S/B>50). For the acquisition period of 73 h, total counts were 53510, of which 1742 were not rejected. The sampling rate of the digital sampling oscilloscope was 20 MHz. The region of interest is indicated by ROI. The scintillation crystal was a commercially available Bicron X—Canberra 802 system.
Figure 2:
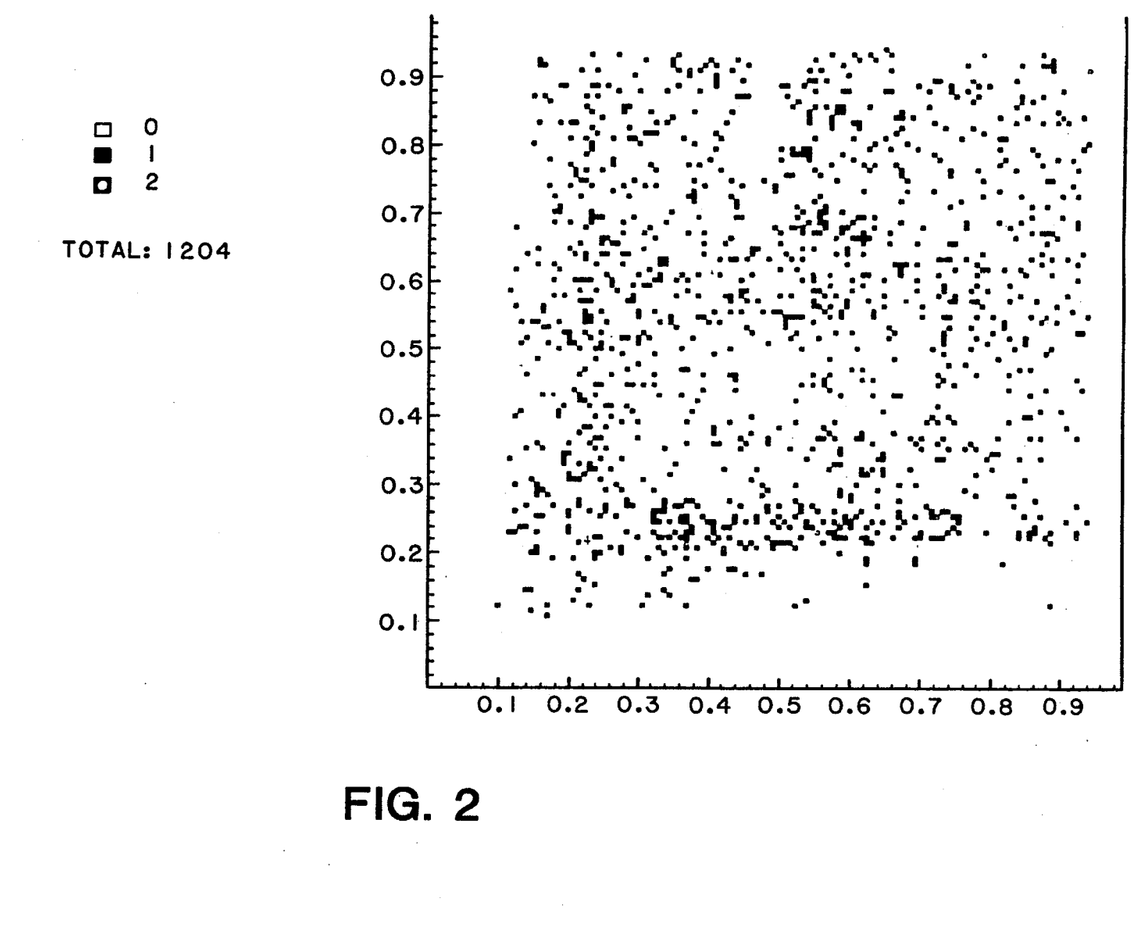
FIG. 2 illustrates the radioactive background (without sample) in a coincident gamma/x-ray detector as in FIG. 1, for 48 hours acquisition time. The total number of triggers was 57073, of which 1204 were not rejected by coincidence and pulse shape analysis. At the energy window where $I^{125}$ is expected (small cross) the count rate is about one count per day.

With coincidence rejection and passive shielding effective, further gains are obtained through pulse shape analysis. This analysis is performed on the output of each scintillation crystal to assess that each constituent of the decay event is compatible with isotopic decay properties, i.e. a 35 keV gamma and one of a few X-rays in the 27–31 keV range for the case of $I^{125}$. Both events should be coincident within nanoseconds and have a pulse shape characteristic of that produced by single photons. This analysis allows discrimination against many other background events originating from charged particles, pile-up of lower energy photons, electronics saturation phenomena and electromagnetic pick-up noise. Knowledge of the electromagnetic pick-up noise is also used to adjust for the DC offset distortions, impose coincidence checks and enhance energy resolution. The implementation of real time pulse analysis normally increases the signal-to-background ratio by more than an order of magnitude. It has culminated in a reduction of background from a few cph to about 1 cpd. The analysis of a 1 picocurie $I^{125}$ with all background measures implemented is shown in FIG. 1.

This type of pulse shape analysis has previously been performed only off-line, and with very expensive electronics. The rationale for using on-line pulse-shape analysis using PC based Digital Storage Oscilloscopes (DSOs) emerged through a series of experiments on three classes of ultralow radioactive background devices. Output was assessed with background rejection by multiple single channel analyzers and computers; threshold/coincidence units and multichannel analyzers (MCAs) combined; and on-line pulse shape analysis with DSOs. The more classical MCA implementations led to a background of a few counts per hour due primarily to electromagnetic pulse pick-up. However, in the same detector/shield system with DSO-based on-line pulse-shape analysis, the background was about one count per day. Thus, pulse shape analysis leads to significant improvement in background rejection.

Another benefit of use of DSOs is that it permits more reliable measurements by checking many parameters not available to MCA-based systems, e.g. bias level. Without any hardware overhead, DSO-based signals permit auto-diagnostics and self-calibration, e.g. real-time monitoring of the performance of high voltage supplies, the gain of PMT's, and the linearity of the data acquisition chain.

It is necessary to emphasize the synergistic roles of all the background reduction measures combined. Without the prior reductions due to coincidence detection, there would be a high and diverse residual background, challenging the computational system. This is particularly important when the CGXD is used to discriminate and quantitate multiple co-resident isotopes. The computational burdens are then much heavier, as the profiles of a decay event must be compared against the allowed profiles for each co-resident isotope. The utility of the surprisingly thick separator only became manifest when the pulse shape analysis program had achieved substantial progress. Previously its positive effects were not evident. While the background reduction achieved by the passive shield and separator together is only a factor of a few, it considerably relieves the computational burden of the DSO/computer system. It will be evident from the following details provided in the Preferred Implementation, that a very substantial effort was necessary to bring the computational burden within the capacities of a low cost PC type computer.

Let us consider the performance of systems which omit one of the above said synergistic background rejection methods. We built series of devices in which only coincidence and pulse shape analysis is used; the observed background is larger than 10 cph. When the composite shielding is not used but one uses coincidence, separator and pulse shape analysis the background is about 1 cph. A similar background is observed when a composite shield is used but the separator is removed. Thus, our experiments show that the background is dominated by radioactive background. The influence of radioactive contamination and Cosmic Rays seems to be comparable. However, electromagnetic and vibrational pick-up are also important at the 10 cph level. In summary, an elimination of any one of the background rejection measures would adversely decrease the effectiveness and increase costs of the entire CGXD system.

These factors are also relevant to specialized CGXD implementations. The DSO based pulse shape analysis is common to all systems. The core disclosed CGXD technology can be implemented in a few basic detector modules with a plurality of prior-art accessories optimized for the specific applications. In the following implementations, only the basic elements are described and many prior-art features are omitted, particularly sample transport and readout display systems.

EXAMPLE 2

Ultralow background CGXD system for $I^{125}$

The detection of gamma rays from $I^{125}$ requires scintillator detectors with reasonable energy resolution. Currently, the best energy resolution is achieved with the NaI(Tl)/PMT combination. However, use of NaI(Tl) leads to an additional hard X-ray background due to the characteristic iodine absorption edge. This is beneficially eliminated by implementing a $CaF_2$/PMT combination.

There is a need to be very selective about the choice of materials to be used in the construction of these devices. All materials which are used in more than 1 mg quantity should be screened for radioactive impurities. More specifically, glass which contains $K^{40}$ should be replaced by quartz or special low background pyrex. Ferric materials are excluded because of radioactive cobalt contamination. Fortunately some types of plastic, e.g. teflon and acrylic, are acceptable, as well as ultrapure copper, tin and lead.

EXAMPLE 3

System for X-rays and high energy gammas.

The case of $I^{125}$ is not typical of many CGX sources because the X-ray energy (27–31 keV) is very close to the gamma ray energy (35 keV). For many CGX sources, however, the gamma ray is in the 200–2,000 keV range, which necessitates some changes in the CGXD construction.

It is usually assumed that energy resolution is limited by the statistics of the scintillation photon emission. However, in practice it is usually limited by the choice of PMT, the bias voltage and the noise of the front-end electronics. Our experience in ultralow background counting of X-ray and gamma ray sources suggests that system optimization is often different at high and low energies. We disclose that at very low count rates, much better energy resolution is possible when the gains of the PMT are low, on the order of a hundred thousand rather than a few million. The optimization of PMT vs. preamplifier gain is very important in order to obtain the best energy resolution and is an important, innovative aspect of the disclosed detection systems.

When the X-ray and gamma energies from the CGX channel differ by factors of a few or more, at least one crystal must be thick enough to absorb all the energy deposited by the gamma. When used to discriminate multiple isotopes, the crystal thickness of a CGXD is determined by the requirement to absorb all of the energy from the most energetic gamma emitted by members of the isotope collection being quantitated. This results in some increase in background for the X-ray detection, as more Cosmic Rays and high energy gammas, e.g. from $K^{40}$, deposit energy in the greater volume of scintillator.

The use of CGX emitters with higher energy gammas leads also to modification of both the separator and the shield. In both cases, the passive shielding device becomes thicker and the fraction of the high atomic number component increases.

The use of CGX emitters with higher energy gammas leads also to changes in software. Different parameters are used in acceptance criteria, especially concerning the pulse width and pulse rise time.

An elegant solution to the X-ray background penalty described above is to place the sample between paired phoswitch detectors. For each detector a 0.1 inch NaI(Tl) or $CaF_2$ scintillator serves well as the slow detector adjacent to the sample. It provides for high energy resolution detection of X-rays, and is substantially transparent to gammas. The backing CsI scintillator serves as the high energy gamma detector. With appropriate pulse-shaping, the DSO based data acquisition system can distinguish if a photon was absorbed in the slow or the fast (NaI) scintillator. Coincidence events can thus be scored, whether the gamma and X-ray are absorbed in a single phoswitch or in both opposed phoswitches.

Additionally, a 4" bismuth germanate (BGO) crystal may be used as an active shield. This implementation should be about four orders of magnitude more sensitive than unshielded or passively shielded devices currently used in hospitals and a factor five to ten better than the system described in Example 1.

EXAMPLE 4

Low background, portable CGXD system using photodiodes
Photodiodes or avalanche photodiodes replace the PMT because of their greater robustness, better stability under temperature variations and lower power requirements. With background rejection by coincidence and pulse shape analysis implemented, less than two kilograms of passive composite shielding is adequate and is not a severe hindrance to portability. Software management is implemented on a laptop computer. Either the opposed detector configuration or the phoswitch format described in Implementation 3 can be utilized.

EXAMPLE 5

Multisample CGXD system using spatially resolving PMT's

Spatially and temporally resolving X-ray/gamma detectors have been built by coupling a single scintillation crystal to a spatially resolving PMT. For example, the Hamamatsu R2486 PMT has four outputs. Measurement of the pulse heights in all four channels allows calculation of the spatial position of the absorbed gamma. Quantitative imaging of 2D sources in contact with the crystal is thus achieved. Good spatial resolution has been achieved only for rather high-intensity sources (1 cps or higher) because of electronic interference noise. This considerable capacitive noise is inherent in these multi-electrode devices, and is complicated by the fact that charge division leads to lower amplitude signals. Thus, artifacts due to EMI influence a spatially resolving PMT more than a simple PMT.

For EC sources arrayed or distributed on a two dimensional membrane support, the core CGXD strategy can still be implemented. The 2D specimen is placed between a non-imaging "hard" detector optimized for the gamma and the imaging PMT. The X-ray is efficiently stopped in the planar scintillator of the imaging scintillator/PMT. An event analysis is triggered by coincident signals from the hard and imaging detectors. DSO pulse shape analysis is performed on each of the four PMT outputs as well as that of the hard detector and requires multiple DSO cards. This analysis is very important because the signals for a large fraction of events are very small and susceptible to electromagnetic and electronic noise, so that decays at one site can be mistakenly attributed to another. The very beneficial net result is an increase in spatial resolution, particularly for low activity sources. Thus sharper images can be obtained and/or controlled sample placements on the support membrane can be closer.

EXAMPLE 6

Gamma and cascade photon coincidence detection

This implementation is designed to capture events in which multiple low energy, cascade photons are emitted during the restructuring of electron shells following electron capture, in coincidence with the gamma from the excited nucleus. The sample is placed between two distinct detector assemblies. A PMT-NaI(T1)-CCD-sample-NaI(T1)-PMT configuration is suggested. In contrast to the prior described implementations, there are considerable complications in data analysis. The totality of events should be analyzed to decide if the event in the CCD is just a UV/visible photon from a cascade or if it results from an X-ray. This requires a very low noise single-photon CCD and may require a cooled device.

Probably a better implementation is one using the following configuration: CCD-gas detector-sample-NaI(T1)-PMT. The gas detector is operated in the self-limited streamer mode, i.e. at the applied high voltage (typically 1000 Volts) a single photon absorption leads to discharge. The gas composition is selected so that the breakdown is not total, leading to spark creation but is limited leading to about 0.2 mm long streamers. The resulting 100,000 amplification in the number of electrons leads to emission of many visible photons. The location of this light pulse is detected by a low noise CCD. Please observe, that it takes a part of a microsecond to develop the streamer. Thus, the gas detector operated in self-limiting mode has a built-in delay, which facilitates its application in coincident systems, e.g. in CGXD.

The experimental difficulty is that the gas detector may be much larger than the size of the CCD. Thus, large focal length optics should be used. To increase the light yield an array of lenslets is placed between the gas detector and CCD. Each of these lenses collimates the divergent light pulse into a flat front or convergent beam.

To improve the photons signal/noise and diminish the detector size, one can use an enhanced CCD, i.e. a combination of a microchannel plate and a CCD. Microchannel plates are available with 10 inch diameter, i.e. about a factor of five larger than the CCD. Thus the image from the gas chamber is projected upon the microchannel plate and the output image is then collimated by an appropriate array of lenses onto the CCD.

The use of a microchannel plate has two further advantages. First, it is an easily gated device and it can be triggered by the high energy photon detected in the NaI(T1)/PMT part of the apparatus. Second, it can be used to match the spectrum between the gas emitter and the CCD detector. More specifically, the input phosphor of the microchannel plate can be optimized to absorb the photons emitted by the gas discharge, whereas the output phosphor will be chosen to match the absorption spectrum of silicon.

EXAMPLE 7

The CGXD system disclosed herein consists of five sub-systems: two photon detectors, e.g. scintillator/photosensor modules; read-out electronics including voltage supplies; a data acquisition and analysis subsystem; a separator/shield subsystem; and a sample holder. Thus, it is essentially the device described in Example 1.

Two scintillation crystals with appropriate photosensors, e.g. PMTs, face each other. They are separated by an appropriate, less than 8 mm separator with a centered biconical hole allowing the sample held therein to irradiate both crystals. The hole dimensions are chosen so that the solid angle of the opening just encompasses the faces of the crystals. This separator optimally limits cross-talk between the crystals and the thickness is necessary to limit certain background events. The crystals are placed in a composite shield which uses a plurality of materials to diminish the background due to ambient radioactivity. This shield, depending on applications, can be from 0.5 to 20 kg in weight.

Energy deposited within the scintillation crystals, e.g. NaI(T1) crystals, is converted into charge pulses by the photosensors and then into voltage pulses that are shaped by fast low-noise preamplifiers. The electronics also include high-voltage power supplies for the photosensors, high-gain amplifiers and a coincidence circuit. Special "triangular shape" shaping preamplifiers are used to permit both fast coincidence and good energy resolution. The signals from both detectors, as well as the coincidence trigger, are inputs to the PC-based digital storage oscilloscope (DSO) card, which is used for fast real-time pulse-shape/pulse-height analysis by software according to the invention.

Development of software supporting the DSO card-based pulse-shape analysis on the PC led to a program with about 30,000 lines of code using three programming languages.

The procedures are coded in Borland Turbo Pascal and C++, which helped to make the code highly modular, transparent and easy to customize. Through changes in the software the same device can be adapted for a variety of applications without hardware changes. The most time-critical procedures are coded in IBM PC assembly language, which enables us to acquire and analyze signals with maximum efficiency.

The DSO card features two inputs with at least 8-bit analog-to-digital convertors (ADC's) and an additional input, which can be used as an acquisition trigger. It should be able to monitor the two input channels simultaneously at a sampling rate of at least 10 MHz. The signals are acquired at a sampling rate of up to 100 megasamples/sec and are continuously stored in the on-board memory until a trigger is detected, whereupon a pre-defined number of post-trigger data points are acquired. Once the acquisition is stopped, the contents of the on-board memory become available for the host computer. Any of the channels can be used as the trigger, and triggering can be also done through software. The sampling rate, the number of post-trigger points, the gains on the channels, and the triggering conditions can be set through a PC I/0 port, while the on-board memory can be accessed directly through a 4 Kbyte window, which allows fast retrieval using the CPU's string instructions or DMA transfer to other peripheral devices.

A pulse produced by a scintillator/PMT or scintillator/photodiode combination when a photon is absorbed has a characteristic shape with an amplitude proportional to the energy deposited by the photon in the scintillator. On the other hand, the shapes of pulses electromagnetically induced in the readout electronics are not so well defined. There are many varieties of the latter, ranging from single narrow spikes, to rapid successions of such spikes, to random electronic noise. In a pulse-height analyzing system spurious pulses may considerably contaminate the acquired spectra and diminish the system's overall signal-to-background ratio. At the same time, many "real" pulses caused by detection of photons are distorted, e.g. when two separate events occur within a short interval of time (pile-up artifacts) or a photon-caused pulse is distorted by a coincident electromagnetic pick-up. Such events blur the acquired spectrum, and should also be either discarded or correctly interpreted based on shape analysis. High-frequency electronic noise in the front end electronics perturbs the spectrum, decreasing energy resolution. The spectrum can be enhanced to the actual resolution of the scintillator through pulse-shape analysis. Without any hardware changes, the software implemented pulse shape analysis enhanced energy resolution by a factor of two for count rates lower than 1 cpm.

I claim:

1. A method for quantifying a coincident gamma/x-ray (CGX) emitter in a sample, comprising:

(a) placing the sample between separate radiation detectors and suppressing background radiation by shielding the detectors in a composite radiation shield and separating the detectors with a separator that absorbs x-rays, (b) and obtaining outputs from the radiation detectors comprising coincident and non-coincident output pulses, the coincident output pulses comprising pulses characteristic of coincident gamma and x-ray emissions from the CGX emitter, (c) analyzing the shape and height of the pulses on-line, (d) discriminating and rejecting non-coincident pulses, (e) discriminating and rejecting coincident pulses that do not match the characteristics of emissions from the CGX emitter, and (f) using the remaining coincident pulses to quantify the presence of as little as 100 pCi of the CGX emitter in the sample, wherein background is reduced to about one count per hour.

2. A method for selective quantitation of a coincident gamma/X-ray (CGX) emitter in a sample, comprising:

(a) placing the sample between separate radiation detectors and obtaining outputs from the radiation detectors comprising coincident and non-coincident output pulses, the coincident output pulses comprising pulses characteristic of coincident gamma and x-ray emissions from the CGX emitter, (b) analyzing the shape and height of the output pulses from the detectors, (c) discriminating and rejecting non-coincident output pulses, (d) discriminating and rejecting coincident output pulses that are not characteristic of coincident gamma/x-ray emissions from the CGX emitter, and (e) using the remaining output pulses to quantify the CGX emitter in the sample.

3. A method according to claim 2, further comprising rejecting background radiation by shielding the detectors in a low radioactive background composite shield.

4. A method according to claim 2, further comprising separating the detectors with a separator that absorbs X-rays.

5. A method according to claim 2, wherein the detectors are opposed along essentially a common axis, and further comprising placing the sample between the detectors.

6. A method according to claim 2, further comprising pre-screening samples without coincidence for activity significantly above gamma background.

7. A method according to claim 2, wherein the method can detect an amount of CGX emitter in the sample of less than 100 picoCurie.

8. A method according to claim 2, wherein the method can detect an amount of CGX emitter in the sample of 1 picoCurie.

9. A method according to claim 2, further comprising the step of selecting the CGX emitter from the isotopes of Lists 1–4.

10. A method according to claim 2, wherein the CGX emitter is an isotope of an element that forms covalent bonds.

11. A method according to claim 2, wherein the CGX emitter is $I^{123}$, $I^{125}$, $I^{126}$, $Br^{76}$, or $Br^{77}$.

12. A method according to claim 2, wherein the CGX emitter is $I^{125}$.

13. A method according to claim 2, wherein the CGX emitter is bound to a chelator conjugated to an organic compound.

14. A method according to claim 2, wherein the CGX emitter is an isotope of the family of CGX lanthanide isotopes.

15. A method according to claim 2, wherein the CGX emitter is adducted to an organic molecule.

16. A method according to claim 2, wherein the method permits detection of less than one attomole of labeled molecule.

17. A method according to claim 2, wherein the CGX emitter is adducted to an organic precursor for the synthesis of a macromolecule.

18. A method according to claim 2, wherein the CGX emitter is adducted to asteroid compound.

19. A method according to claim 2, wherein the CGX emitter is adducted to estrogen.

20. A method according to claim 2, wherein the CGX emitter is adducted to a protein.

21. A method according to claim 2, wherein the CGX emitter is coupled to a precursor of nucleic acids.

22. A method according to claim 2, wherein the CGX emitter is incorporated in a primer for nucleic acid elongation.

23. A method according to claim 22, further comprising using the primer in an in vitro nucleic acid amplification protocol.

24. A method according to claim 22, further comprising using the primer in the polymerase chain reaction (PCR) process.

25. A method according to claim 22, wherein the polymerase chain reaction is stopped while the amplification is still exponential.

26. A method according to claim 22, wherein the primer is used in a linear polymerase reaction.

27. A method according to claim 15, wherein the organic molecule is a monoclonal or polyclonal antibody or an antigen.

28. A method according to claim 15, wherein the organic molecule is used in a competitive assay.

29. A method according to claim 27, wherein an antibody is used to detect cancerous cells in a physiological sample.

30. A method according to claim 19, wherein the level of estrogen and other steroids in physiological fluids is used to diagnose breast cancer.

31. A method according to claim 2, wherein the CGX emitter is coupled to a unicellular organism.

32. A method according to claim 2, wherein the CGX emitter is coupled to a virus, a bacterial cell, an algae cell, a fungal cell, or a protozoa.

33. A method according to claim 32, wherein the virus is an agent of sexually or blood transfusion transmitted disease, and the bacteria is tubercular bacillus or bacteria which are precursors of sexually transmitted diseases.

34. A method according to claim 28, wherein the competitive assay is used to detect contamination of human physiological fluids.

35. A method according to claim 34, wherein the physiological fluid is blood, urine, sputum, tear drops, sweat, amniotic fluid or spinal fluid.

36. A method according to claim 28, wherein the competitive assay is used to detect contamination of animal physiological fluids.

37. A method according to claim 28, wherein the competitive assay is used to detect contamination of food and agricultural products.

38. A method according to claim 37, wherein the contamination is the presence of microorganisms and their toxic byproducts.

39. A method according to claim 38, wherein the contamination comprises aflatoxins or mycotoxins.

40. A method according to claim 28, wherein the competitive assay is used to detect contamination of samples of water, soil or air from the environment.

41. A method according to claim 40, wherein the competitive assay is used to detect chemical contamination.

42. A method according to claim 28, wherein the competitive assay is performed upon airborne substances in a clean room environment, and data are used to estimate the number and size distribution of micron sized dust and other particulates suspended in the air.

43. A method according to claim 2, wherein at least one of the detectors is a Ge-semiconducting detector optimized for detection of X-rays.

44. A method according to claim 43, wherein the Ge-detector is less than 0.5 inch thick and uses a cryostat with thin beryllium or aluminum windows.

45. A method according to claim 2, wherein at least one of the detectors is a spatially resolving gas detector.

46. A method according to claim 45, wherein the spatially resolving detector is a thin self-limiting streamer chamber, and the spatial resolution is obtained by imaging, using a CCD camera.

47. A method according to claim 2, wherein at least one of the detectors comprises a scintillator and photosensor.

48. A method according to claim 47, wherein the scintillator is doped NaI or $CaF_2$ crystal with a thickness less than 0.5 inch.

49. A method according to claim 47, wherein a photomultiplier is used to amplify the signal from the scintillator.

50. A method according to claim 47, wherein a large surface photodiode or avalanche photodiode is used to amplify the signal from the scintillator.

51. A method according to claim 49, further comprising amplifying the resulting signal at high gain.

52. A method according to claim 47, wherein a low radioactive background quartz window is placed between the scintillator and photosensor.

53. A method according to claim 47, wherein the scintillator is housed in a low radioactive background housing.

54. A method according to claim 53, wherein the housing is less than 0.1 $g/cm^2$ in thickness and is made of very low atomic number elements having low radioactive background.

55. A method according to claim 54 wherein the housing comprises beryllium, aluminum, or plastic.

56. A method according to claim 2, further comprising shielding the detector within a shield comprising a very high atomic number metal (Z>61).

57. A method according to claim 56, wherein the high atomic number material is lead, tungsten, or mercury.

58. A method according to claim 2, further comprising shielding the detector within a shield comprising subsequent layers of materials with low atomic number, medium atomic number, and high atomic number, with the high atomic number layer being the most external.

59. A method according to claim 58, wherein the materials with low and medium atomic number are highly purified copper (Cu) and tin (Sn), respectively.

60. A method according to claim 2, further comprising absorbing the majority of external X-rays by placing a separator between the separate radiation detectors.

61. A method according to claim 60, wherein the separator comprises a layer of a high atomic number material (Z>61) with a thickness larger than 2 mm.

62. A method according to claim 61, wherein the separator is cladded on both surfaces with thin layers of materials with low atomic number and medium atomic number.

63. A method according to claim 62, wherein the low and medium atomic number materials are highly purified copper (Cu) and tin (Sn), respectively.

64. A method according to claim 60, further comprising providing a biconical hole in the separator, and placing the sample in the hole.

65. A method according to claim 60, further comprising the step of placing the sample in a sample holder comprising a narrow microcapillary ended with a spherical, hollow tip containing up to 0.1 cc of liquid, and placing the sample holder in the separator.

66. A method according to claim 60, wherein the sample holder consists essentially of material with both very low atomic number and low radioactive background.

67. A method according to claim 60, wherein the sample holder comprises beryllium, aluminum, or plastic.

68. A method according to claim 60, wherein the separator has a plurality of conical holes ordered into an easily distinguished pattern, and samples to be studied are placed into the holes.

69. A method according to claim 60, further comprising the step of blotting the samples upon an appropriate thin film with patterns substantially identical to the hole pattern in the separator, and aligning the blotted film with the separator between the detectors.

70. A method according to claim 69, wherein the separator consists of two parts, each with identical hole patterns, and the blotted film is placed between these two parts.

71. A method according to claim 2, further comprising amplifying the pulse from the scintillator with low noise preamplifiers, shaping the pulse into a characteristic triangular pulse with rise time shorter than 200 nsec and fall time between 0.5 and 5 microseconds, and matching the pulse shapes and amplitudes in both crystals to better than 10%.

72. A method according to claim 71, wherein the preamplifiers are two stage preamplifiers.

73. A method according to claim 2, further comprising analyzing each pulse for amplitude by appropriate single channel analyzers (SCA), and using the SCA outputs in a coincidence circuit (COINC) with a well defined time window.

74. A method according to claim 73, further comprising analyzing the shape of each pulse in an analog-to-digital converter (ADC) or digital storage oscilloscope (DSO) sampling at a rate of at least 10 MHz per channel, using the signal from the coincidence circuit as trigger.

75. A method according to claim 74, further comprising storing pulse shape records from the ADC or DSO in the fast memory of a computer for further data analysis.

76. A method according to claim 75, further comprising analysing each pulse shape record by at least one software module having acceptance criteria, rejecting a pulse on-line if it does not satisfy the acceptance criteria of all the software modules, and counting the pulse if it satisfies the acceptance criteria of all the software modules.

77. A method according to claim 76, wherein the software modules comprise:

a) analyzer of pulse amplitude;
b) analyzer of the total pulse width;
c) analyzer of the shape of the rising part of the pulse;
d) analyzer of the shape of the falling part of the pulse;
e) analyzer of the delay between the pulses from the two detectors;
f) analyzer of pulse multiplicity;
g) analyzer of the pre-pulse trace; and
h) comparator of the pulse shape with a standard high energy photon pulse shape using a least squares technique;

individually or in combination.

78. A method according to claim 76, further comprising selecting coincident pulses to build a three dimensional scatter plot matrix, and using the matrix to further optimize background rejection.

79. A method according to claim 47, further comprising coupling at least one of the scintillators with a spatially resolving photomultiplier tube, amplifying the output pulses from the photomultiplier tube by at least two matched low noise amplifiers, and using the outputs as inputs to a multichannel analog-to-digital converter or digital storage oscilloscope module.

80. A method according to claim 79, in which four matched low noise amplifiers are used.

81. A method according to claim 80, and further comprising analytically comparing the amplified pulses from the spatially resolving photomultiplier tube with standard shape pulses, and using only events satisfying the standard shape condition in both photomultiplier tube outputs are used to build 1D or 2D images.

82. A method according to claim 2, wherein at least one of the detectors is a phoswitch module comprising a gamma detector consisting of two optically coupled scintillators with different characteristic response times.

83. A method according to claim 82, wherein the phoswitch comprises a very thin scintillator with high energy resolution, closer to the sample, and a thick, high stopping power scintillator, and the two scintillators are separated by a few millimeters of optically transparent material with low radioactive background.

84. A method according to claim 83, wherein the scintillator with high energy resolution comprises NaI(Tl) or $CaF_2(Eu)$, the thick, high stopping power scintillator comprises CsI or BGO, and the optically transparent material comprises acrylic plastic or quartz.

85. A method according to claim 82, wherein the signal from the phoswitch is amplified by a fast, low noise shaping amplifier and then analyzed on-line by data analysis modules comprising a) analyzer of pulse amplitude;
b) analyzer of the total pulse width;
c) analyzer of the shape of the rising part of the pulse;
d) analyzer of the shape of the falling part of the pulse;
e) analyzer of the delay between the pulses from the two detectors;
f) analyzer of pulse multiplicity;
g) analyzer of the pre-pulse trace; and
h) comparator of the pulse shape with a standard high energy photon pulse shape using a least squares technique;

individually or in combination, and the pulse shape analysis is used to localize the scintillator element inside the phoswitch within which the photon is absorbed.

86. The method of claim 2, wherein a plurality of different CGX emitters are separately detected in a sample.

87. The method of claim 2, further comprising transporting the sample to the detector, and providing a readout display.

88. The method of claim 2, wherein the CGX emitter is introduced in the human body.

89. The method of claim 2, wherein the CGX emitter is introduced into the environment as a tracer.

90. The method of claim 27, wherein the antigen or antibody is used in a radioimmunoassay.

91. The method of claim 1, wherein the shield is an active shield comprising a bismuth germanate crystal.

* * * * *